United States Patent [19]
Graves et al.

[11] Patent Number: 5,510,551
[45] Date of Patent: Apr. 23, 1996

[54] EXTRACTION OF CAROTENOIDS FROM NATURAL SOURCES

[75] Inventors: Frederic A. Graves, Ham Lake; Daniel D. Gallaher, Roseville, both of Minn.

[73] Assignee: Humanetics Corporation, St. Louis Park, Minn.

[21] Appl. No.: 208,985

[22] Filed: Apr. 28, 1994

Related U.S. Application Data

[63] Continuation of Ser. No. 12,314, Feb. 2, 1993, which is a continuation of Ser. No. 684,590, Apr. 12, 1991, Pat. No. 5,245,095.

[51] Int. Cl.$^6$ ............................ C07C 403/00; C07C 7/00
[52] U.S. Cl. ............................ 585/351; 585/854; 585/855
[58] Field of Search .................................. 585/351, 854, 585/855

[56] References Cited

U.S. PATENT DOCUMENTS

| | | |
|---|---|---|
| 2,170,872 | 8/1939 | Peebles . |
| 2,511,824 | 6/1950 | Miller . |
| 2,543,083 | 2/1951 | White et al. . |
| 2,572,467 | 10/1951 | Gebhart . |
| 2,615,927 | 10/1951 | Passino . |
| 2,652,433 | 9/1953 | Blaizot . |
| 2,708,627 | 5/1955 | Toulmin, Jr. . |
| 2,717,210 | 9/1955 | De Witte . |
| 2,741,643 | 4/1956 | Jones et al. . |
| 2,741,644 | 10/1956 | Blaizot . |
| 2,848,508 | 8/1958 | Barnett et al. . |
| 2,861,891 | 11/1958 | Bauernfeind et al. . |
| 2,959,522 | 11/1960 | Zajic . |
| 3,001,912 | 9/1961 | Miescher . |
| 3,039,877 | 6/1962 | Borenstein . |
| 3,268,606 | 8/1966 | Jaeger . |
| 3,274,072 | 9/1966 | Burdick . |
| 3,906,112 | 9/1975 | Anderson . |
| 3,920,834 | 11/1975 | Klaui et al. . |
| 4,380,553 | 4/1983 | Schmidt . |
| 4,439,629 | 5/1984 | Ruegg . |
| 4,680,314 | 7/1987 | Nonomura . |
| 4,713,398 | 12/1987 | Nonomura . |

FOREIGN PATENT DOCUMENTS

| | | |
|---|---|---|
| 52-18218 | 5/1977 | Japan . |
| 776405 | 6/1957 | United Kingdom .. |
| WO86/04059 | 7/1986 | WIPO . |

OTHER PUBLICATIONS

WPI Abstract, Access No. 66-20662F/00 Apr. 9, 1963.
WPI Abstract, Access No. 72-76913T/48 Apr. 9, 1938.

Primary Examiner—Sharon Gibson
Attorney, Agent, or Firm—Faegre & Benson

[57] ABSTRACT

A carotenoid-enriched fraction is extracted from natural sources, such as carrots, by (i) separating the carotenoid-containing natural source into a carotenoid-containing liquid fraction and a pulp fraction, (ii) adding a carotenoid precipitation agent including calcium chloride, calcium hydroxide, calcium lactate or calcium gluconate to the liquid fraction to form a carotenoid-enriched solid precipitate, and (iii) separating the carotenoid-enriched solid precipitate from the carotenoid-depleted liquid portion.

8 Claims, 2 Drawing Sheets

EXTRACTION OF CAROTENOIDS FROM NATURAL SOURCES

This is a continuation of U.S. patent application Ser. No. 08/012,314, filed 02 Feb. 1993 which is a continuation of U.S. patent application Ser. No. 07/684,590, filed 12 Apr. 1991 which issued as U.S. Pat. No. 5,245,095 on 14 Sep. 1993.

FIELD OF THE INVENTION

Broadly, the invention relates to the extraction of carotenoids from carotenoid-containing natural sources. Specifically, the invention relates to the extraction of carotenoids from a natural source, such as carrots, by juicing the carrots, treating the juice with a carotenoid precipitation agent including calcium chloride, calcium hydroxide, calcium lactate, calcium gluconated potassium hydroxide or magnesium chloride to produce a carotenoid-enriched solid precipitate portion and a carotenoid-depleted liquid portion, and separating the solid and liquid portions.

BACKGROUND

Carotenoids are a class of naturally occurring pigments found in trace amounts in the tissues of higher plants, algae, bacteria and fungi. Carotenoids are polyenes having a $C_{40}$ carbon skeleton (phytoene) which contains an extended network of single and double bonds. The various carotenoids are formed by chemically modifying this $C_{40}$ carbon skeleton. For example, dehydrogenation of phytoene yields the carotenoid lycopene which is responsible for the color of tomatoes and cyclization of both ends of lycopene yields the carotenoid β-carotene which is responsible for the color of carrots.

Carotenoids, such as β-carotene, are valuable pigments useful for coloring various comestibles, such as margarine, as they avoid the health concerns associated with synthetic pigments and actually possess significant nutritional value (β-carotene is a precursor to the formation of retinal and vitamin A in humans).

Because carotenoids occur naturally in only trace amounts, the carotenoids must be extracted in concentrated form in order to be useful. Ordinarily, carotenoids are extracted from natural sources by treating the material with a carotenoid-solubilizing hydrocarbon solvent, such as hexane, or chloroform, separating the carotenoid-containing hydrocarbon solvent from the remainder of the material, and then driving off the hydrocarbon solvent to produce a carotenoid-enriched solid product.

In addition to carotenoids, plants contain a variety of other constituents which are soluble in hydrocarbon solvents such as various proteins and lipids. Accordingly, the carotenoid-enriched solid product typically includes significant amounts of other components in addition to the carotenoid(s).

Use of a hydrocarbon solvent to extract the carotenoids significantly increases the cost and complexity of the extraction procedure due to the cost of the hydrocarbon solvent, the cost of removing the hydrocarbon-solvent from the final product, the cost of recovering the removed hydrocarbon solvent, and the cost of disposing of contaminated hydrocarbon solvent which cannot be reused. In addition, use of a hydrocarbon solvent to effect extraction of carotenoids results in significant environmental damage due to the release of hydrocarbon fumes into the atmosphere and the need to dispose of contaminated hydrocarbon solvent which cannot be reused.

Accordingly, a substantial need exists for a simple and environmentally safe process of extracting carotenoids from carotenoid-containing natural sources which avoids the need to utilize a hydrocarbon solvent.

SUMMARY

We have discovered a process for extracting carotenoids from carotenoid-containing natural sources, such as carrot juice, which includes the steps of (i) separating the carotenoid-containing natural source into a carotenoid-containing liquid fraction and a pulp fraction, (ii) contacting the liquid fraction with an effective fractionating amount of a carotenoid precipitation agent including calcium chloride, calcium hydroxide, calcium lactate, calcium gluconate, potassium hydroxide or magnesium chloride so as to fractionate the liquid fraction into a carotenoid-enriched solid precipitate portion and a carotenoid-depleted liquid portion, and (iii) separating the carotenoid-enriched solid portion from the carotenoid-depleted liquid portion.

The carotenoid-enriched solid fraction may be utilized directly or may be further purified so as to separate the carotenoid(s) from the other constituents in the solid fraction by any suitable separation technique. Preferred techniques including chemical and enzymatic hydrolysis and chemical and enzymatic degradation whereby the noncarotenoid constituents are rendered separable from the carotenoid(s) in an aqueous media. While the carotenoid-enriched solid fraction may be purified utilizing conventional organic liquid or solid phase extraction, use of such an extraction procedure destroys the desired organic solventless nature of the process and therefore is not favored.

DETAILED DESCRIPTION OF THE INVENTION INCLUDING A BEST MODE

Figure 1:
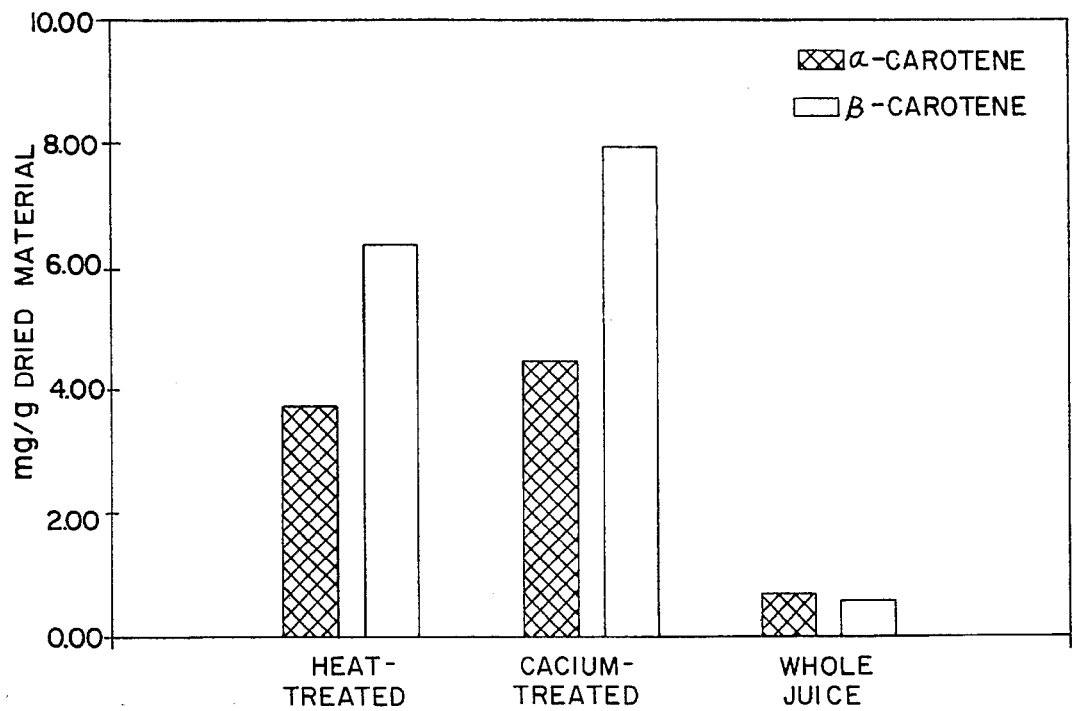
FIG. 1 is a bar graph obtained from the data in Table One indicating the concentration of carotene recovered from treated and untreated carrot juice.

A carotenoid-enriched solid product may be simply, quickly and efficiently extracted from carotenoid-containing natural sources, such as carrots, by (i) separating the carotenoid-containing natural source into a carotenoid-containing liquid fraction and a pulp fraction, (ii) treating the carotenoid-containing liquid fraction with a carotenoid precipitation agent including calcium chloride, calcium hydroxide, calcium lactate, calcium gluconate, potassium, hydroxide or magnesium chloride so as to fractionate the liquid fraction into a carotenoid-enriched solid precipitate portion and a carotenoid-depleted liquid portion, and (iii) separating the liquid and solid portions by conventional means.

We believe that substantially any carotenoid-containing natural source may be effectively fractionated in accordance with the invention to produce a carotenoid-enriched product including specifically, but not exclusively, fruits such as pineapples and oranges; vegetables such as carrots, spinach, sweetpotatoes and tomatoes; algae such as Dunaliella Salina; bacteria such as those of the order Mucorales including C. trispora and Blakeslea Circinans; and fungi. Based upon ease of availability, low cost, and high concentration of commercially valuable β-carotene, the starting material of preference is carrots.

The first step in the process of the invention is to separate the carotenoid-containing natural source into a carotenoid-containing liquid fraction and a pulp fraction. While the exact mechanism employed to achieve this separation depends upon several factors, including the specific carotenoid source, such separation can typically be achieved by simply juicing the carotenoid source and filtering the juice through a course-mesh filter. Disruption of the cell structure of the carotenoid source during separation generally inherently results in transfer of the carotenoid(s) in the carotenoid source from the pulp fraction to the liquid fraction.

Addition of a carotenoid precipitation agent including calcium chloride, calcium hydroxide, calcium lactate, calcium gluconate, potassium hydroxide or magnesium chloride to the carotenoid-containing liquid fraction causes precipitation of a carotenoid-enriched fraction which may be separated from the remaining carotenoid-depleted liquid fraction by conventional separation methods.

The physical and/or chemical mechanism(s) responsible for such precipitation of a carotenoid-enriched solid fraction by the addition of a source of ionizable calcium is not fully understood. In an effort to ascertain whether the pectin and/or proteins contained in the liquid fraction participate in this phenomena, samples of carrot juice were treated with a protease enzyme and a pectinase enzyme prior to addition of the carotenoid precipitation agent calcium chloride (See Table Three and accompanying conclusions). Such pretreatment with an enzyme to degrade the proteins (protease) and pectin (pectinase) contained in the juice resulted in no noticeable alteration in fractionation of the juice by the calcium chloride. Accordingly, it appears that the proteins and pectin contained in the carotenoid-containing liquid fraction do not play an independently active role in the physical and/or chemical mechanism responsible for precipitation of a carotenoid-enriched solid fraction from the liquid fraction by the addition of the listed carotenoid precipitation agents.

Figure 2:
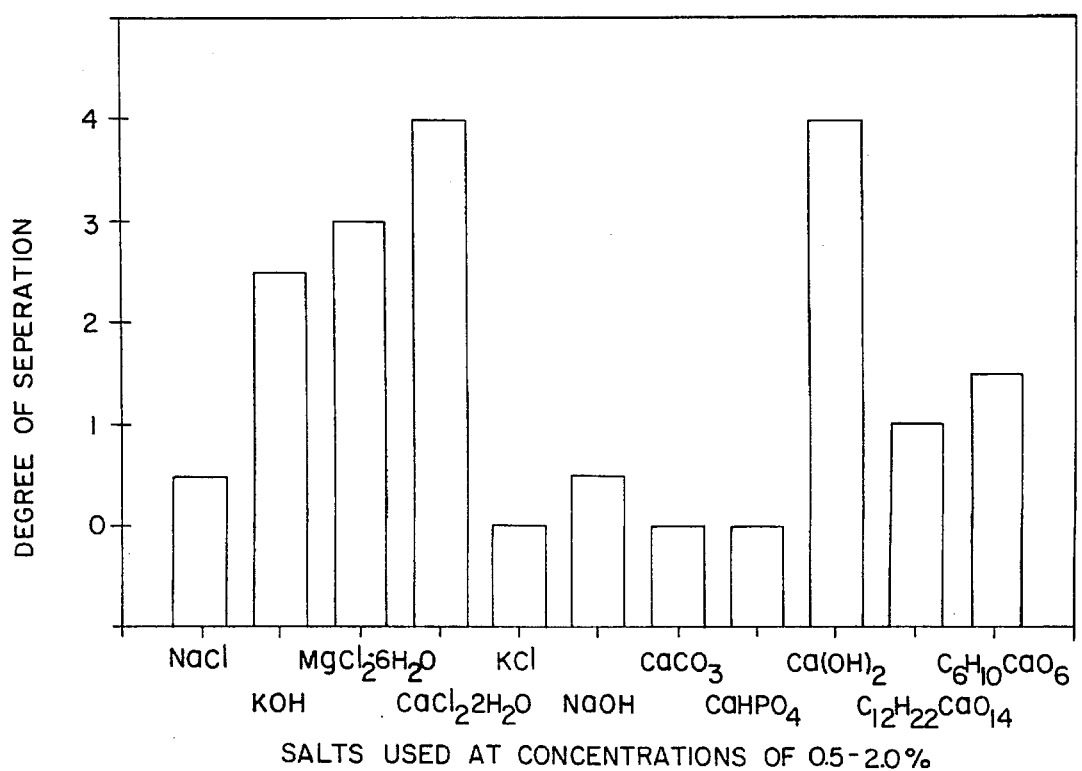
FIG. 2 is a bar graph indicating the degree of carotenoid separation achieved by the addition of from 0.5 to 2 wt % of various salts to whole carrot juice with the highest degree of separation obtained for each salt within the tested concentration range reported on the graph.

Efforts to obtain comparable fractionation with other mineral salts such as sodium chloride, potassium chloride, magnesium chloride, calcium carbonate, and calcium phosphate; and caustics such as sodium hydroxide and potassium hydroxide have proven substantially unsuccessful (See FIG. 2 and Protocol-salt treatment). Accordingly, it appears that the only reagents capable of providing effective fractionation are those capable of providing ionized calcium under those conditions present in the juice, such as calcium chloride, calcium hydroxide, calcium lactate and calcium gluconate, with calcium chloride appearing to provide significantly better separation at lower concentrations.

Figure 3:
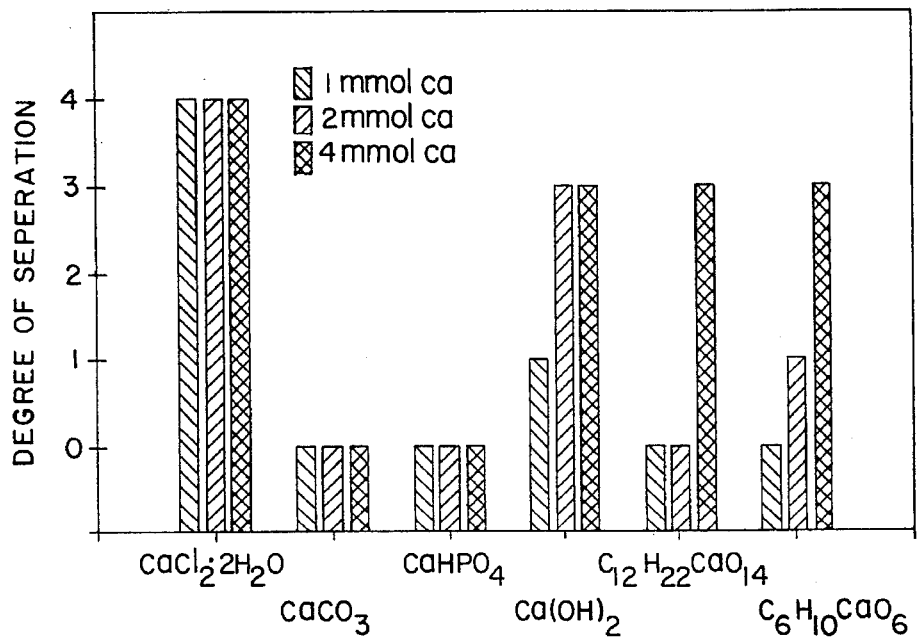
FIG. 3 is a bar graph indicating the degree of carotenoid separation achieved by the addition of various concentrations of calcium salts to whole carrot juice.

Referring to FIG. 3, superior separation of the carotenoids into a distinct solid precipitate portion may be achieved from a carotenoid-containing liquid fraction of a carotenoid-containing natural source by adding calcium chloride at concentrations of from about 0.01 to 10 wt %, preferably about 0.05 to 3 wt %, calcium hydroxide at concentrations of from 0.01 to 10 wt %, preferably about 0.05 to 3 wt %, calcium lactate at concentrations of from about 2 to 10 wt %, preferably about 2 to 4 wt %, and calcium gluconate at concentrations of from about 4 to 10 wt %, preferably about 4 to 6 wt %, with the best overall separation achieved with calcium chloride.

Referring to FIG. 1 and Table One, the liquid fraction may be significantly fractionated by heating the liquid fraction to temperatures of at least 60° C.

Separation of the liquid fraction by treating with the listed carotenoid precipitation agents in accordance with the process of the invention may be achieved under ambient conditions. However, for the purpose of increasing the rate of separation, the liquid fraction is preferably heated to a temperature above about 40° C. and preferably between about 40° to 60° C. while being treated with one of the listed carotenoid precipitation agents.

Effective fractionation may be obtained by treating the liquid fraction with one of the listed carotenoid precipitation agents for as little as about one minute (See Table Two and accompanying comments). While several factors may affect the optimum contact period such as the specific carotenoid precipitation agent employed, the concentration of the carotenoid precipitation agent, the temperature of the liquid fraction, and the type of carotenoid-containing source, effective fractionation generally occurs in less than one hour, and more specifically in less than thirty minutes. Generally, optimum fractionation appears to be achieved for carrot juice heated to slightly elevated temperatures and treated with one of the listed carotenoid precipitation agents at a contact period of about five to ten minutes. Contact periods of less than about five minutes result in a slightly less effective separation while contact periods of greater than about ten minutes produce little additional separation.

It is believed that optimal fractionation may also be obtained by treating the liquid fraction with one of the listed carotenoid precipitation agents for less than about five minutes, possibly less than about one minute, by employing temperatures between about 80°–120° C.

Figure 4:
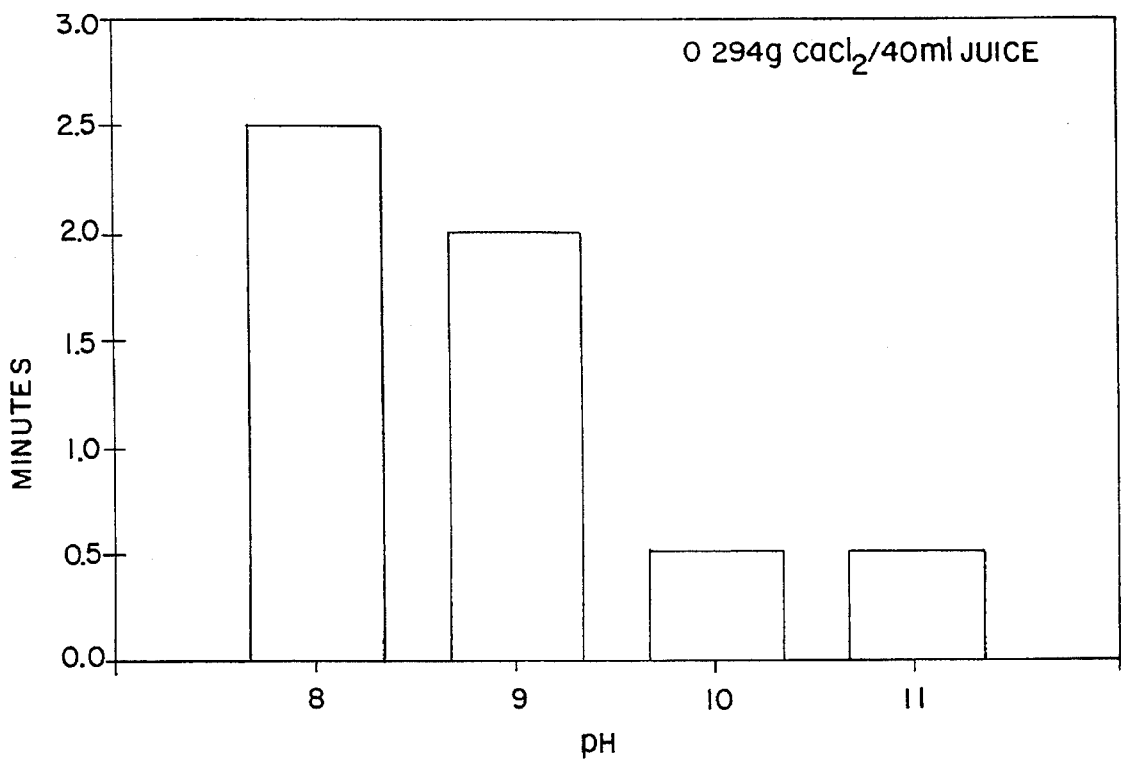
FIG. 4 is a bar graph indicating the speed of carotenoid separation achieved by the addition of calcium chloride to whole carrot juice at various pH levels.

Referring to FIG. 4 and Table Four, the pH of the liquid fraction can affect the rate of separation and overall separation efficiency. Carrot Juice has a natural pH of about 6.0. Carrot juice having a pH adjusted with NaOH as necessary to between about 6 to 7 appears to provide the most complete separation (clearer liquid fraction) while that adjusted to between about 10 to 11 appears to provide nearly instantaneous separation after addition of the carotenoid precipitation agent.

Separation of the carotenoid-enriched solid precipitate portion from the carotenoid-depleted liquid portion may be achieved by any conventional method, including centrifugation/decantation/freeze-drying, centrifugation/decantation/heat drying, heat drying, evaporation, and the like.

The solid carotenoid-enriched portion may be utilized without further processing wherever the pigmentation provided by the concentrated carotenoid(s) is desired. If desired, the carotenoid-enriched solid portion may be further refined to separate the carotenoid(s) from the other precipitated components such as ash, carbohydrates, lipids, and proteins, and obtain a more concentrated carotenoid-containing product by employing conventional purification techniques such as chemical and enzymatic hydrolysis, chemical and enzymatic degradation, liquid-liquid extraction, solid phase extraction, etc.

Comparative Testing Protocol

Carrots were juiced with a disintegrator and the juice separated from the pulp by centrifugation or pressing. The juice was divided into three 40 ml samples and placed into 125 ml Erlenmeyer flasks. A first of the samples was left untreated. A second of the samples was heated by submerging the sample into a waterbath maintained at 60° C. for twenty minutes. A third of the samples was treated with calcium chloride dihydrate and then heated by submerging the sample into a waterbath maintained at 60° C. for twenty minutes.

The samples were centrifuged for 15 minutes at 2000×g to produce a solid pellet and a liquid supernatant. The supernatant was decanted from the solid pellet and the pellet freeze-dried. The freeze-dried pellets were analyzed for $\alpha$ and $\beta$-carotene concentrations using HPLC technology in accordance with the HPLC Protocol set forth below.

Testing Protocol

HPLC

Freeze-dried pellets were pulverized with a mortar and pestle. Approximately 0.025 grams of each sample were added to 4 milliliters of water. This mixture was then extracted with three 10 milliliter portions of a combination of petroleum ether:acetone (50:50 v/v) and filtered through a Buchner funnel. The filer cake was discarded and the filtrate evaporated to dryness under nitrogen. The resulting dried extract was resuspended in 4 milliliters of pure chloroform. A 1 milliliter sample of the resuspended extract was diluted with 4 milliliters of chloroform. The diluted extract was filtered through a 0.45 um filter and then analyzed by high performance liquid chromatography (HPLC) in accordance with the procedure set forth in *Journal of Food Science*, Vol 52, No. 3, pp. 744–46, 1987 for $\alpha$ and $\beta$-carotene content.

Sample carotene content was quantified by comparison of peak areas with peak areas of authentic standards of known concentration obtained from Sigma Chemical Co. Standard concentrations used were 12.5, 25.0, 50.0, and 100.0 ug/ml.

The milligrams of $\alpha$ and $\beta$ carotene per gram of dried solid material are set forth in FIG. 1.

Testing Protocol

Salt Treatment with Various Salts

Carrots were juiced with a disintegrator and the juice separated from the pulp by centrifugation or pressing. The juice was divided into 40 ml samples and placed into 125 ml Erlenmeyer flasks. Individual samples were treated with a salt selected from sodium chloride, potassium hydroxide, magnesium chloride hexahydrate, calcium chloride dihydrate, potassium chloride, sodium hydroxide, calcium carbonate, calcium phosphate, calcium hydroxide, calcium lactate and calcium gluconate at concentrations of 0.5, 1.0 and 2.0 wt % for sixty minutes. The extent of separation was observed and recorded in accordance with the nomenclature set forth below.
Nomenclature 0=No separation 1=Slight separation 2=Fair separation 3=Good separation 4=Excellent separation The best degree of separation attained for each of the salts, at the tested concentrations, is plotted in FIG. 2.

The treated samples were centrifuged for 15 minutes at 20° C. and 2000×g to produce a solid pellet and a liquid supernatant. The supernatant was decanted from the solid pellet and the pellet freeze-dried.

Testing Protocol

Salt Treatment with Calcium Salts

Carrots were juiced with a disintegrator and the juice separated from the pulp by centrifugation or pressing. The juice was divided into 40 ml samples and placed into 125 ml Erlenmeyer flasks. Duplicate samples were treated with a calcium salt selected from calcium chloride dihydrate, calcium carbonate, calcium phosphate, calcium hydroxide, calcium lactate and calcium gluconate at concentrations of 1, 2 and 4 mmoles for sixty minutes. The extent of separation was observed and recorded in accordance with the nomenclature set forth below.
Nomenclature 0=No separation 1=Slight separation 2=Fair separation 3=Good separation 4=Excellent separation The degree of separation attained for each of the calcium salts at each concentration level is plotted in FIG. 3.

The treated samples were centrifuged for 15 minutes at 25° C. and 2000×g to produce a solid pellet and a liquid supernatant. The supernatant was decanted from the solid pellet and the pellet freeze-dried.

Testing Protocol

Heating and Salt Treatment

Carrots were juiced with a disintegrator and the juice separated from the pulp by centrifugation or pressing. The juice was divided into 40 ml samples and placed into 125 ml Erlenmeyer flasks. The samples were treated with a salt of the type (Salt-type) and in the amount (Salt-grams) set forth in Table Two and immersed in a constant temperature water bath heated to 60° C. for the period of time (Contact Time) set forth in Table Two. The extent of separation was observed and recorded in accordance with the nomenclature set forth below.
Nomenclature 0=No separation 1=Slight separation 2=Fair separation 3=Good separation 4=Excellent separation The treated samples were centrifuged for 15 minutes at 25° C. and 2000×g to produce a solid pellet and a liquid supernatant. The supernatant was decanted from the solid pellet and the pellet freeze-dried.

Testing Protocol

Heating, Salt and Enzyme Treatment

Carrots were juiced with a disintegrator and the juice separated from the pulp by centrifugation or pressing. The juice was divided into 40 ml samples and placed into 125 ml Erlenmeyer flasks. The samples were treated with an enzyme of the type (Enzyme-type) and in the amount (Enzyme-grams) set forth in Table Three. The enzyme containing sample was immersed in a constant temperature water bath heated to the temperature set forth in Table Three (Bath Temp) for the period of time set forth in Table Three (Contact Time Heat+Enzym). The enzyme/heat treated samples were treated with a salt of the type (Salt-type) and in the amount (Salt-grams) set forth in Table Three for the period of time (Contact Time-Salt) set forth in Table Three. The extent of separation was observed and recorded in accordance with the nomenclature set forth below.

Nomenclature

0=No separation

1=Slight separation

2=Fair separation

3=Good separation

4=Excellent separation

The treated samples were centrifuged for 15 minutes at 25° C. and 2000×g to produce a solid pellet and a liquid supernatant. The supernatant was decanted from the solid pellet and the pellet freeze-dried.

Testing Protocol

CaCl and pH Treatment

Carrots were juiced with a disintegrator and the juice separated from the pulp by centrifugation or pressing. The juice was divided into 40 ml samples and placed into 125 ml Erlenmeyer flasks. The pH of the samples were adjusted to 8, 9, 10 or 11 with a solution of 10N NaOH and then treated with 0.294 g of calcium chloride dihydrate for thirty minutes. Excellent separation was observed for all samples. The length of time required to achieve excellent separation after addition of the Calcium chloride was recorded.

Nomenclature

0=No separation

1=Slight separation

2=Fair separation

3=Good separation 4 1 =Excellent separation

The treated samples were centrifuged for 15 minutes at 25° C. and 2000×g to produce a solid pellet and a liquid supernatant. The supernatant was decanted from the solid pellet and the pellet freeze-dried.

Testing Protocol

Heating, Salt and pH Treatment

Carrots were Juiced with a disintegrator and the juice separated from the pulp by centrifugation or pressing. The juice was divided into 40 ml samples and placed into 125 ml Erlenmeyer flasks. The pH of the samples were adjusted as set forth in Table Four with a solution of 10N NaOH, treated with 0.294 g of calcium chloride dihydrate, and then immersed in a constant temperature water bath heated to 60° C. for ten minutes. Excellent separation was observed for all samples. The extent of separation was observed and recorded in accordance with the nomenclature set forth below.

The treated samples were centrifuged for 15 minutes at 25° C. and 2000×g to produce a solid pellet and a liquid supernatant. The supernatant was decanted from the solid pellet and the pellet freeze-dried.

TABLE One

Comparison of Carotene Concentrations
Heat Treated/Calcium Treated/Untreated Carotene

| # | Bath Temp (°C.) | Contact Time in Bath (min) | Salt (type) | Salt (mmoles) | α (mg/g) [mg/L] | β (mg/g) [mg/L] | Total (mg/g) [mg/L] |
|---|---|---|---|---|---|---|---|
| 100 | — | — | — | — | (0.679) [72.0] | (0.683) [72.5] | (1.362) [144.5] |
| 101 | 60 | 20 | — | — | (3.73) [46.75] | (6.40) [80.0] | (10.13) [126.75] |
| 102 | 60 | 20 | CaCl$_2$ | 2 | (4.48) [56.0] | (7.96) [99.5] | (12.44) [155.5] |

TABLE Two

Heat + Inorganic Salts

| # | Contact Time (min) | Salt (type) | Salt (grams) | Separtn |
|---|---|---|---|---|
| 200a | 20 | CaCl$_2$ | (0.294) | 4 |
| 200b | 20 | CaCl$_2$ | (0.294) | 4 |
| 201a | 20 | Ca(OH)$_2$ | (0.148) | 4 |
| 201b | 20 | Ca(OH)$_2$ | (0.148) | 4 |
| Cntrl | 10 | — | — | 4 |
| Cntrl | 10 | — | — | 4 |
| Cntrl | 20 | — | — | 4 |
| Cntrl | 20 | — | — | 4 |
| 210a | 05 | CaCl$_2$ | (0.147) | 4 |
| 210b | 05 | CaCl$_2$ | (0.147) | 4 |
| 211a | 10 | CaCl$_2$ | (0.147) | 4 |
| 211b | 10 | CaCl$_2$ | (0.147) | 4 |
| 212a | 20 | CaCl$_2$ | (0.147) | 4 |
| 212b | 20 | CaCl$_2$ | (0.147) | 4 |
| 213a | 05 | CaCl$_2$ | (0.294) | 4 |
| 213b | 05 | CaCl$_2$ | (0.294) | 4 |
| 214a | 10 | CaCl$_2$ | (0.294) | 4 |
| 214b | 10 | CaCl$_2$ | (0.294) | 4 |
| 215a | 20 | CaCl$_2$ | (0.294) | 4 |
| 215b | 20 | CaCl$_2$ | (0.294) | 4 |
| 216a | 05 | CaCl$_2$ | (0.544) | 4 |
| 216b | 05 | CaCl$_2$ | (0.544) | 4 |
| 217a | 10 | CaCl$_2$ | (0.544) | 4 |
| 217b | 10 | CaCl$_2$ | (0.544) | 4 |
| 218a | 20 | CaCl$_2$ | (0.544) | 4 |
| 218b | 20 | CaCl$_2$ | (0.544) | 4 |

| Trial | #Comments |
|---|---|
| 200a/b | Separation was excellent. Supernatant very clear and pellets very firm. Decantation was very easy. |
| 201a/b | Separation was excellent. Pellets were very firm. Decantation was very easy. |

TABLE Three

| | | Heat + Inorganic Salts + Enzymes | | | | | | |
|---|---|---|---|---|---|---|---|---|
| # | Bath Temp (°C.) | Contact Time (Heat + Enzym) (hrs) | Contact Time (Salt) (hrs) | Salt (type) | Salt (grams) | Enzyme (type) | Enzyme (grams) | Separtn |
| 300a | 40° | 05[bb] | 05[c] | CaCl$_2$ | (0.4) | Protease | (0.004) | 4 |
| 300b | 40° | 05[bb] | 05[c] | CaCl$_2$ | (0.4) | Protease | (0.004) | 4 |
| 310a | 30° | 18[b] | 01[cc] | CaCl$_2$ | (0.147) | Pectinase | (1 ml) | 4 |
| 310b | 30° | 18[b] | 01[cc] | CaCl$_2$ | (0.147) | Pectinase | (1 ml) | 4 |

Observations:

Treatment of a 40 ml sample of whole carrot juice with 0.01 wt % protease (incubation at 40° C. for 5 hours) produced no visible separation. Subsequent addition of 0.0027 moles of Ca$^{++}$ in the form of CaCl$_2$•2H$_2$O produced rapid separation resulting in a clearer supernatant moiety and a lower viscosity carotenoid moiety than typically achieved. This indicates that degradation of the protein present in whole carrot juice does not effect separation of carotenoids when used alone but can assist in acheiving greater separation when used in conjunction with calcium treatment.

Treatment of a 40 ml sample of whole carrot juice with 0.01 wt % pectinase (incubation at 30° C. for 18 hours) produced no visible separation. Subsequent addition of 0.001 moles of Ca$^{++}$ in the form of CaCl$_2$•2H$_2$O initiated separation within three minutes resulting in a clear supernatant moiety and a well defined carotenoid moiety within one hour. This indicates that degradation of the pectin present in whole carrot juice does not effect separation of carotenoids when used alone but can assist in hastening separation when used in conjunction with calcium treatment.

TABLE Four

| | Heat + Inorganic Salt w/pH Adjustment | | | | | |
|---|---|---|---|---|---|---|
| # | pH Reading | Bath Temp (°C.) | Contact Time (min) | Salt (type) | Salt (grams) | Separtn |
| Cntrl | — | — | — | — | — | 0 |
| Cntrl | — | — | — | — | — | 0 |
| 400a | 6.50 | 60° | 10 | CaCl$_2$ | (0.294) | 4 |
| 400b | 6.50 | 60° | 10 | CaCl$_2$ | (0.294) | 4 |
| 401a | 7.00 | 60° | 10 | CaCl$_2$ | (0.294) | 4 |
| 401b | 7.00 | 60° | 10 | CaCl$_2$ | (0.294) | 4 |
| 402a | 8.00 | 60° | 10 | CaCl$_2$ | (0.294) | 4 |
| 402b | 8.00 | 60° | 10 | CaCl$_2$ | (0.294) | 4 |
| 403a | 9.00 | 60° | 10 | CaCl$_2$ | (0.294) | 4 |
| 403b | 9.00 | 60° | 10 | CaCl$_2$ | (0.294) | 4 |
| 404a | 10.00 | 60° | 10 | CaCl$_2$ | (0.294) | 4 |
| 404b | 10.00 | 60° | 10 | CaCl$_2$ | (0.294) | 4 |
| 405a | 11.00 | 60° | 10 | CaCl$_2$ | (0.294) | 4 |
| 405b | 11.00 | 60° | 10 | CaCl$_2$ | (0.294) | 4 |

[b]Sample under constant agitation at 87 cycles/min during immersion in water bath.
[bb]Sample under constant agitation at 85 cycles/min during immersion in water bath.
[c]Sequence: Enzyme and Salt added to sample with subsequent heat treatment.
[cc]Sequence: Enzyme and Salt added with period of heat treatment occuring inbetween.

Trial #s with same tens diget (110s, 120s, etc) indicate that trials were conducted employing same source of carrot juice. Trial #s differing only as to designation (a) (b) indicates pair of identically treated samples.

The specification, including the examples, is intended to aid in a complete and unlimited understanding of the invention. Since various embodiments of the invention may be made without departing from the spirit and scope of the invention, the scope of the invention lies in the claims hereinafter appended.

We claim:

1. A process for extracting carotenoids from a carotenoid-containing natural source without the use of a hydrocarbon solvent, which comprises the steps of:

(a) separating a natural source of a carotenoid into a carotenoid-containing liquid fraction and a pulp fraction, (b) contacting the liquid fraction with an effective fractionating amount of a hydrocarbon solvent free precipitating agent selected for the group consisting of potassium hydroxide and magnesium chloride so as to fractionate the liquid fraction into a carotenoid-enriched solid precipitate portion and a carotenoid-depleted liquid portion wherein both the solid and liquid portions are free or hydrocarbon solvent, and (c) separating the carotenoid-enriched solid portion from the carotenoid-depleted liquid portion without the use of a hydrocarbon solvent so as to form a carotenoid-enriched solid extract which has not been contacted with a hydrocarbon solvent during extraction.

2. The process of claim 1 wherein the liquid fraction is contacted with about 0.01 to about 10 wt % precipitating agent.

3. The process of claim 1 wherein the liquid fraction is contacted with the precipitating agent under ambient conditions.

4. The process of claim 3 wherein the liquid fraction is contacted with the precipitating agent for a time period of about 10 to 30 minutes.

5. The process of claim 1 wherein the natural source is carrots.

6. The process of claim 1 wherein the liquid fraction is contacted with about 0.05 to about 2 wt % precipitating agent.

7. The process of claim 1 wherein the liquid fraction is contacted with the precipitating agent at a temperature about about 40° C.

8. The process of claim 1 wherein the pH of the liquid fraction is between about 6 to 8.

* * * * *

UNITED STATES PATENT AND TRADEMARK OFFICE
CERTIFICATE OF CORRECTION

PATENT NO.    :    5,510,551

DATED         :    April 23, 1996

INVENTOR(S)   :    Frederic A. Graves and Daniel D. Gallaher

It is certified that error appears in the above-identified patent and that said Letters Patent is hereby corrected as shown below:

Col. 1, Line 18, delete "gluconated", insert -- gluconate, --

Col. 2, Line 63, between "potassium" and "hydroxide", delete ","

Col. 4, Line 41, delete "Juice", insert -- juice --

Col. 7, Line 56, delete "1"

Col. 7, Line 65, delete "Juiced", insert -- juiced --

UNITED STATES PATENT AND TRADEMARK OFFICE
CERTIFICATE OF CORRECTION

| | | |
|---|---|---|
| PATENT NO. : | 5,510,551 | |
| DATED : | April 23, 1996 | |
| INVENTOR(S) : | Frederic A. Graves and Daniel D. Gallaher | |

It is certified that error appears in the above-identified patent and that said Letters Patent is hereby corrected as shown below:

Col. 8, Table One, move "Contact" down one line

Col. 8, Table One, insert after last line -- Observation: Both heat-treatment and calcium-treatment of carrot juice produce a coagulam that is highly enriched in $\alpha$ and $\beta$ carotene. Most of the $\alpha$ and $\beta$ carotene in the whole juice is recovered by these processes. Heat treatment combined with calcium treatment appears to increase the total amount of carotene ($\alpha$ and $\beta$) recovered by about 23% over that recovered by heat treatment only. --

Col. 9, Lines 55-60, insert -- = -- after "b", "bb", "c", and "cc"

Col. 10, Line 31, delete "for", insert -- from --

Col. 10, Line 58, delete "about", insert -- above --

Signed and Sealed this

Fifth Day of November, 1996

*Attest:*

BRUCE LEHMAN

*Attesting Officer*     *Commissioner of Patents and Trademarks*